United States Patent
Lee et al.

(10) Patent No.: US 9,928,589 B2
(45) Date of Patent: Mar. 27, 2018

(54) APPARATUS AND METHOD FOR SUPPORTING ACQUISITION OF MULTI-PARAMETRIC IMAGES

(71) Applicant: Samsung Electronics Co., Ltd., Suwon-si (KR)

(72) Inventors: Ki-Yong Lee, Suwon-si (KR); Yeong-Kyeong Seong, Yongin-si (KR); Jong-Ha Lee, Yongin-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 60 days.

(21) Appl. No.: 14/146,359

(22) Filed: Jan. 2, 2014

(65) Prior Publication Data
US 2014/0185900 A1    Jul. 3, 2014

(30) Foreign Application Priority Data
Jan. 2, 2013 (KR) .................. 10-2013-0000301

(51) Int. Cl.
| | |
|---|---|
| *G06K 9/00* | (2006.01) |
| *G06T 7/00* | (2017.01) |
| *G06F 19/00* | (2018.01) |

(52) U.S. Cl.
CPC .......... *G06T 7/0014* (2013.01); *G06F 19/345* (2013.01); *G06F 19/321* (2013.01); *G06F 19/3406* (2013.01)

(58) Field of Classification Search
CPC ............... G06T 7/0012; G06T 7/0081; G06T 2207/30004; G06T 2207/30008; G06T 2207/10072; G06T 2207/10081; G06T 2207/10104; G06T 2207/10108; G06T 2207/10112; G06T 2207/20112; G06T 2207/20212
USPC ................................................ 382/128–132
See application file for complete search history.

(56) References Cited

U.S. PATENT DOCUMENTS

| | | | |
|---|---|---|---|
| 6,547,727 B1* | 4/2003 | Hashiguchi | A61B 10/00 128/920 |
| 6,690,961 B1* | 2/2004 | Kaufman | A61B 5/055 324/307 |
| 6,887,200 B2 | 5/2005 | Hashiguchi et al. | |
| 7,860,551 B2 | 12/2010 | Sugimoto | |
| 8,188,743 B2 | 5/2012 | Sugiura | |
| 8,194,937 B2 | 6/2012 | Chen | |
| 8,198,891 B2 | 6/2012 | Sacolick et al. | |
| 8,208,703 B2 | 6/2012 | Kawagishi et al. | |

(Continued)

FOREIGN PATENT DOCUMENTS

| | | |
|---|---|---|
| CN | 101076724 A | 11/2007 |
| JP | 2000-262479 A | 9/2000 |

(Continued)

*Primary Examiner* — Wesley Tucker
(74) *Attorney, Agent, or Firm* — Jefferson IP Law, LLP

(57) ABSTRACT

An apparatus and a method for supporting acquisition of a multi-parametric image are provided. An apparatus for supporting acquisition of a multi-parametric image includes: a disease selector configured to select a suspected disease of a patient based on patient information; and an image selector configured to determine a set of imaging conditions of a multi-parametric magnetic resonance image corresponding to the suspected disease based on a multi-parametric magnetic resonance imaging model.

25 Claims, 9 Drawing Sheets

(56) References Cited

U.S. PATENT DOCUMENTS

| | | | |
|---|---|---|---|
| 2002/0097902 A1* | 7/2002 | Roehrig | A61B 6/032 382/132 |
| 2004/0122790 A1 | 6/2004 | Walker et al. | |
| 2006/0064396 A1* | 3/2006 | Wei | A61B 6/463 |
| 2008/0097186 A1* | 4/2008 | Biglieri | A61B 5/055 600/407 |
| 2008/0285830 A1* | 11/2008 | Hong | G06T 7/0012 382/131 |
| 2009/0006132 A1 | 1/2009 | Avinash et al. | |
| 2011/0066024 A1* | 3/2011 | Shih | G06F 19/321 600/410 |
| 2012/0278359 A1 | 11/2012 | Igarashi | |
| 2014/0153795 A1* | 6/2014 | Lenox | G06T 7/0012 382/128 |

FOREIGN PATENT DOCUMENTS

| | | |
|---|---|---|
| JP | 2006-095278 A | 4/2006 |
| JP | 2009-056109 A | 3/2009 |
| JP | 2009-207527 A | 9/2009 |
| JP | 2012-157688 A | 8/2012 |

\* cited by examiner

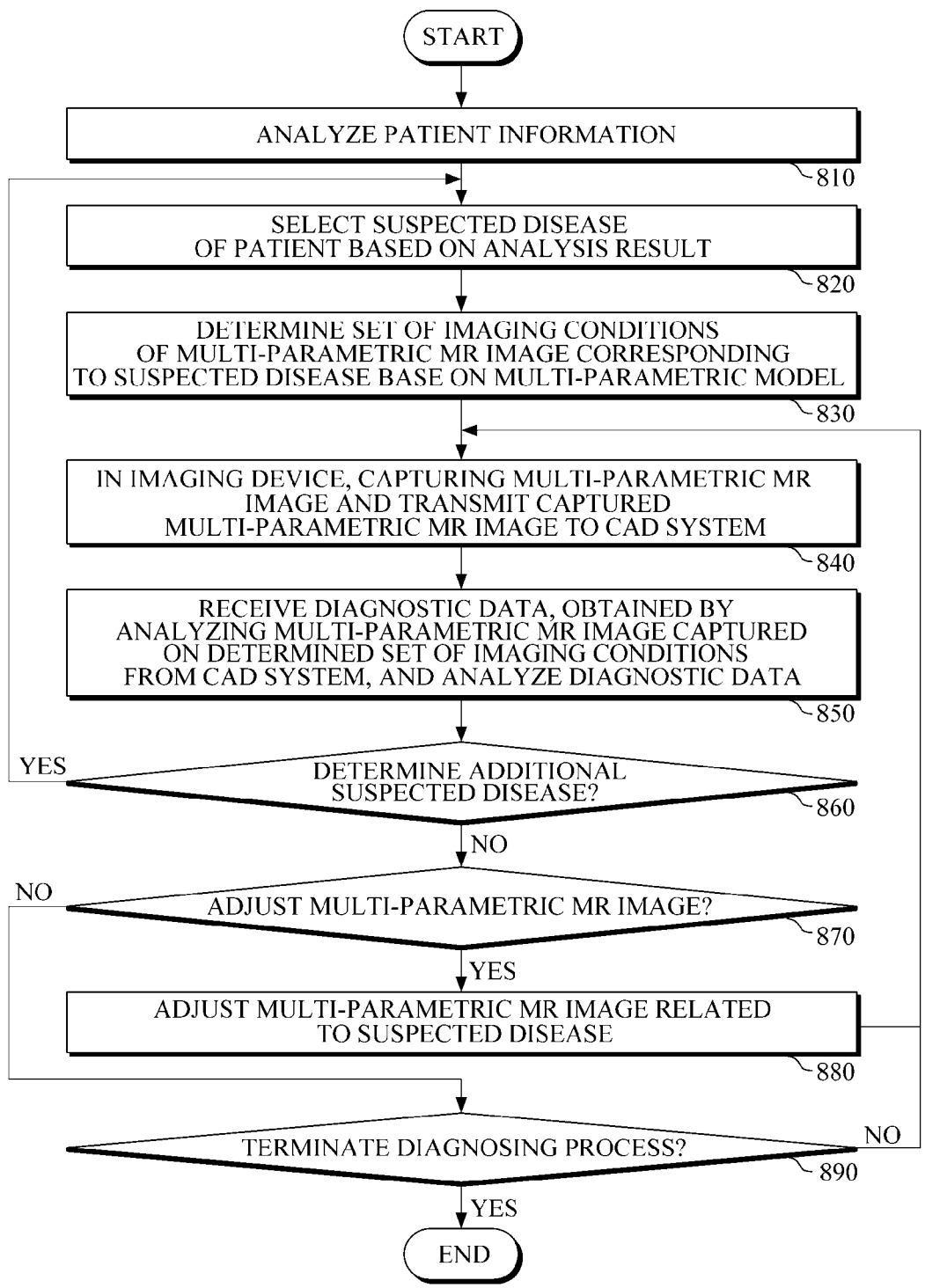

APPARATUS AND METHOD FOR SUPPORTING ACQUISITION OF MULTI-PARAMETRIC IMAGES

CROSS-REFERENCE TO RELATED APPLICATION

This application claims the benefit under 35 U.S.C. § 119(a) of a Korean Patent Application No. 10-2013-0000301 filed on Jan. 2, 2013, in the Korean Intellectual Property Office, the entire disclosure of which is incorporated herein by reference for all purposes.

BACKGROUND

1. Field

The following description relates to an apparatus and a method for supporting acquisition of a multi-parametric magnetic resonance (MR) image based on characteristics of a patient.

2. Description of Related Art

Magnetic resonance imaging (MRI) is a medical imaging technique used in radiology to take MR images. MR images are cross-sectional images of the body that are obtained by utilizing the phenomenon of nuclear magnetic resonance. The body contains countless protons ($^1$H nuclei), the spin of which may be flipped by absorption of electromagnetic waves of certain frequency. The excitation and relaxation of the protons by the absorption and emission of electromagnetic waves within a positive field is referred to as proton magnetic resonance. An MRI signal refers to electromagnetic wave that is emitted from the protons during the relaxation. An MR image is obtained by visualizing the MRI signals from protons that are distributed inside the body. Various techniques exist for taking an MR image, and the selection of different imaging parameters and variables may result in images having different contrast between different body tissues.

An MR image may be weighted by various types of contrast, including proton density, T1 (spin-lattice relaxation time), T2 (spin-spin relaxation time), magnetic susceptibility, chemical shift, chemical exchange, diffusion of water molecule and elasticity. The different contrast-type images are taken by using specific set of imaging parameters. Thus, many images of different contrast may be acquired of one region of the body using a method for acquiring multi-parametric images by adjusting the weights and variables used to obtain the image.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an apparatus for supporting acquisition of a multi-parametric magnetic resonance image, the apparatus including an image selector configured to determine a set of imaging conditions of a multi-parametric MR image corresponding to a suspected disease of a patient based on a multi-parametric MRI model.

The general aspect of the apparatus may further include a disease selector configured to analyze patient information to determine one or more candidate diseases and to select the suspected disease of the patient based on a probability of each of the candidate diseases.

The disease selector may include a genetic information analyzer that is configured to select one or more candidate diseases based on patient genetic information using a disease susceptibility model.

The disease selector may include an electronic mandatory record (EMR) analyzer that is configured to select one or more candidate diseases based on EMR information using a disease susceptibility model.

The disease selector may include a diagnosis-aiding information analyzer that is configured to select one or more candidate diseases based on diagnosis-aiding information input by a user.

The image selector may be configured to determine the set of imaging conditions by determining at least one of location, direction, distance, imaging order and imaging parameters of the multi-parametric MR image based on the multi-parametric MRI model.

The multi-parametric MRI model may include an image type and an imaging order for each disease, the multi-parametric MRI model being established in advance by analyzing priority of multi-parametric MR images for each disease.

In another general aspect, there is provided an apparatus for supporting acquisition of a multi-parametric MR image, the apparatus including: a diagnostic data analyzer configured to receive diagnostic data generated by a computer aided diagnosis (CAD) system by analyzing a captured multi-parametric MR image, and to analyze the received diagnostic data; and an image adjuster configured to, according to an analysis result of the received diagnostic data, determine an additional set of imaging conditions or adjust an existing set of imaging conditions for a multi-parametric MR image related to the suspected disease.

The diagnostic data analyzer may be configured to receive the diagnostic data from the CAD system in real time.

The diagnostic data may include body regions susceptible to one or more diseases and a disease susceptibility of each of the body regions.

In another general aspect, there is provided an apparatus for supporting acquisition of a multi-parametric MR image, the apparatus including: a disease selector configured to select a suspected disease of a patient based on patient information; an image selector configured to determine a set of imaging conditions of a multi-parametric MR image that corresponds to the suspected disease based on a multi-parametric MRI model; a diagnostic data analyzer configured to receive diagnostic data generated by a CAD system by analyzing the selected multi-parametric MR image, and to analyze the received diagnostic data; and an image adjuster configured to, according to an analysis result of the received diagnostic data, adjust the multi-parametric MR image based on the suspected disease.

The image adjuster may be configured to determine an additional set of imaging conditions for the multi-parametric MR image related to the suspected disease according to the analysis result.

The image adjuster may be configured to adjust an existing set of imaging conditions for the multi-parametric MR image related to the suspected disease according to the analysis result.

The disease selector may be configured to select an additional suspected disease according to the analysis result, and the image selector is configured to select a multi-parametric MR image related to the additional suspected disease.

The patient information may include at least one selected from the group consisting of genetic information, EMR information, and diagnosis-aiding information input by a user.

In another general aspect, there is provided an apparatus for supporting acquisition of a multi-parametric MR image, the apparatus including: an image selector configured to select a set of imaging conditions of a multi-parametric MR image based on patient medical information using a database that associates imaging conditions with medical conditions.

The general aspect of the apparatus may further include: a disease selector configured to determine a suspected disease of the patient from the patient medical information, in which the image selector is configured to select the set of imaging conditions based on the suspected disease of the patient.

The set of imaging conditions may include at least one selected from the group consisting of a location, a direction, a distance, an imaging order, and an imaging parameter for taking a multi-parametric MR image; and the patient medical information may include at least one selected from the group consisting of genetic information, EMR information, diagnosis-aiding information input by a user, a diagnostic data from a CAD system and a medical image of the patient.

The suspected disease of a patient may be obtained from a CAD system based on a previous medical image of the patient.

In another general aspect, there is provided an MRI apparatus including: an imaging unit configured to obtain a multi-parametric MR image of the patient using the set of imaging conditions selected by the image selector of the apparatus for supporting acquisition of a multi-parametric MR image described above.

In another general aspect, there is provided a method for supporting acquisition of a multi-parametric MR image, the method involving: determining a set of imaging conditions of a multi-parametric MR image that corresponds to a suspected disease of a patient, based on a multi-parametric MRI model.

The general aspect of the method may further involve: determining one or more candidate diseases by analyzing patient information; and selecting the suspected disease of the patient based on a probability of each of the candidate diseases.

The patient information may include genetic information, and the determination of one or more candidate diseases comprises selecting one or more candidate diseases based on the genetic information using a disease susceptibility model.

The patient information may include EMR information, and the determination of one or more candidate diseases comprises determining one or more candidate diseases based on the EMR information using a disease susceptibility model.

The patient information may include diagnosis-aiding information input by a user, and the determination of one or more candidate diseases comprises determining one or more candidate diseases based on the diagnosis-aiding information.

The set of imaging conditions may include at least one of location, direction, distance, imaging order and imaging parameters of the multi-parametric MR image.

The multi-parametric MRI model may include an image type and an imaging order for each disease, the multi-parametric MRI model being established in advance by analyzing priority of multi-parametric MR images for each disease.

In another general aspect, there is provided a method for supporting acquisition of a multi-parametric MR image, the method involving: receiving diagnostic data obtained by analyzing an acquired multi-parametric MR image from a CAD system, and analyzing the diagnostic data; and according to an analysis result of the diagnostic data, determining an additional set of imaging conditions for a multi-parametric MR image or adjusting an existing set of imaging conditions for a multi-parametric MR image.

The receiving of the diagnostic data may involve receiving the diagnostic data from the CAD system in real time.

The diagnostic data may include body regions susceptible to one or more diseases and a disease susceptibility of each of the body regions.

In another general aspect, there is provided a method for supporting acquisition of a multi-parametric MR image, the method involving: selecting a suspected disease of a patient based on patient information; determining a set of imaging conditions of a multi-parametric MR image that corresponds to the suspected disease based on a multi-parametric MRI model; receiving diagnostic data obtained by analyzing the multi-parametric MR image from a CAD system, and analyzing the diagnostic data; and adjusting the multi-parametric MR image based on an analysis result of the diagnostic data.

The adjusting of the multi-parametric MR image may involve, according to the analysis result of the diagnostic data, determining an additional set of imaging conditions for the multi-parametric MR image related to the suspected disease.

The adjusting of the multi-parametric MR image may involve, according to the analysis result of the diagnostic data, adjusting the determined set of imaging conditions for the multi-parametric MR image related to the suspected disease.

The adjusting of the multi-parametric MR image may involve, according to the analysis result of the diagnostic data, selecting an additional suspected disease of the patient and determining an additional set of imaging conditions.

The selecting of the additional suspected disease may involve, according to the analysis result of the diagnostic data, determining the additional suspected disease of the patient, and the determining of the additional set of imaging conditions comprises determining a set of imaging conditions for a multi-parametric MR image related to the additional suspected disease.

The patient information may include at least one selected from the group consisting of genetic information, EMR information and diagnosis-aiding information input by a user.

In another general aspect, there is provided a method for supporting acquisition of a multi-parametric MR image, the method involving selecting a set of imaging conditions of a multi-parametric MR image based on patient medical information using a database stored in a memory.

The set of imaging conditions may include at least one selected from the group consisting of a location, a direction, a distance, an imaging order, and an imaging parameter for taking a multi-parametric MR image; and the patient medical information may include at least one selected from the group consisting of genetic information, EMR information, diagnosis-aiding information input by a user, a diagnostic data from a CAD system and a medical image of the patient.

The selecting of the set of imaging conditions may involve determining a suspected disease of a patient based on the patient medical information, and selecting the set of imaging conditions based on the suspected disease.

The suspected disease of the patient may be obtained from a CAD system based on a previous medical image of the patient.

The general aspect of the method may further involve: obtaining a multi-parametric MR image of the patient using the selected set of imaging conditions; analyzing the obtained multi-parametric MR image of the patient to either adjust the selected set of imaging conditions or to select another set of imaging conditions; and obtaining another multi-parametric MR image of the patient using the adjusted set of imaging conditions or the another set of imaging conditions.

Other features and aspects will be apparent from the following detailed description, the drawings, and the claims.

BRIEF DESCRIPTION OF THE DRAWINGS

FIG. 8 is a flow chart illustrating an example of a method for supporting acquisition of a multi-parametric MR image using an apparatus shown in FIG. 5.

Figure 1:
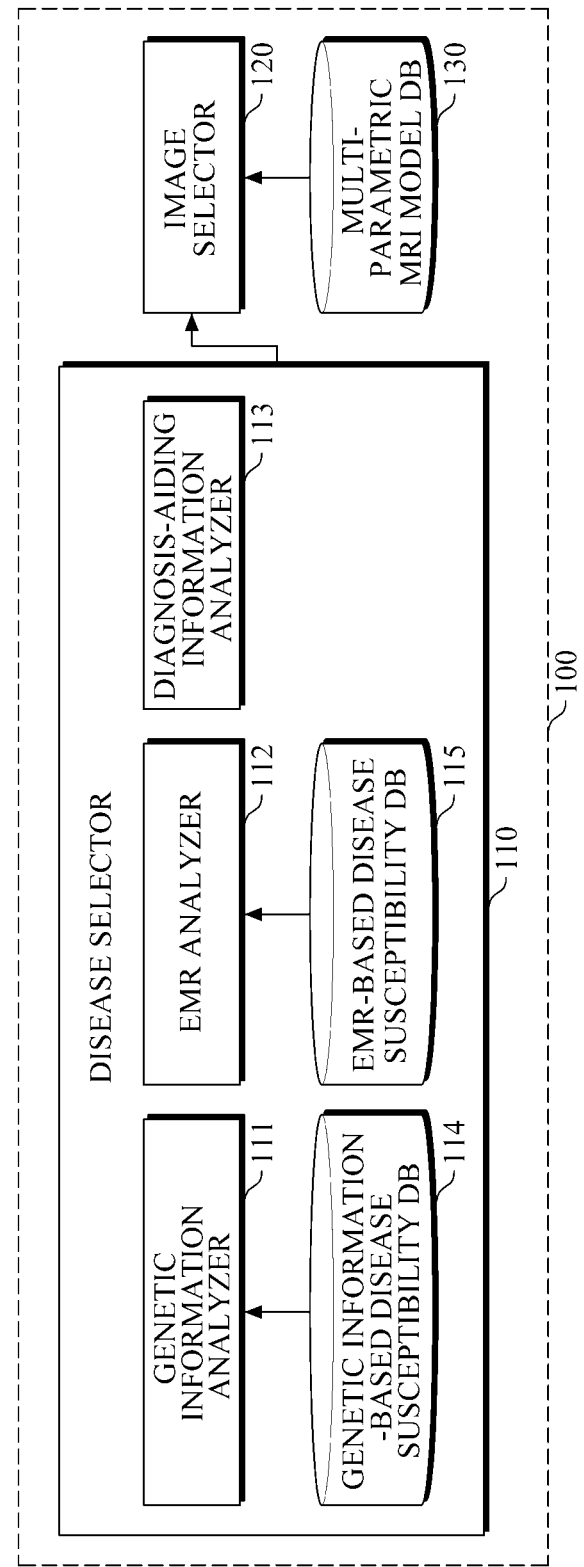
FIG. 1 is a block diagram illustrating an example of an apparatus for supporting acquisition of a multi-parametric MR image.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

As described above, an MR image may be weighted by various types of contrast, including proton density, T1 (spin-lattice relaxation time), T2 (spin-spin relaxation time), magnetic susceptibility, chemical shift, chemical exchange, diffusion of water molecule and elasticity. The different contrast-type images are taken by using specific set of imaging parameters. Thus, many images of different contrast may be acquired of one region of the body using a method for acquiring multi-parametric images by adjusting the weights and variables used to obtain the image.

Thus, the MRI technology is capable of producing multi-parametric images based on various physical properties, and the ability to accurately diagnose a medical condition may be further improved by analyzing the multi-parametric images. However, the optimal type of contrast that may be used to take an MR image for a specific disease is still determined heavily based on heuristics on a case by case basis.

Hereinafter, various examples of apparatuses and methods for supporting acquisition of a multi-parametric MR image will be described with references to accompanying drawings. The examples of methods and apparatuses for supporting acquisition of a multi-parametric MR image may be implemented with a hardware component, a software component, or a combination thereof that is separate from a Computer-Aided Diagnosis (CAD) system. A CAD system assists doctors in interpreting a medical image by performing a computational analysis of the medical image. However, the present disclosure is not limited thereto. In some examples, the hardware and software components of the apparatus for supporting acquisition of a multi-parametric MR image may be shared as an element of a CAD system.

FIG. 1 is a block diagram illustrating an example of an apparatus for supporting acquisition of a multi-parametric MR image.

Referring to the example illustrated in FIG. 1, an apparatus 100 for supporting acquisition of a multi-parametric MR image includes a disease selector 110 and an image selector 120.

The disease selector 110 selects a suspected disease that a patient may be suffering from, by analyzing information regarding a patient. The patient information may include genetic information, electronic medical record (EMR) information, and diagnosis-aiding information input by a user, such as a doctor. The EMR information is computerized information about the patient, such as personal information, a history of illness, a health condition, a medical record and a hospitalization record. The diagnosis-aiding information refers to various types of information, including a body region that is susceptible to a disease, a body region of which a multi-parametric MR image is captured, and a set of imaging conditions, which is determined by a doctor during a check-up of the patient.

The disease selector 110 may also include a genetic information analyzer 111, an EMR analyzer 112, a diagnosis-aiding-information analyzer 113, a genetic-information-based disease susceptibility model database 114 and an EMR-based disease susceptibility model database 115. Using the above configurations of the disease selector, the disease selector 110 may analyze the patient information, and may determine a suspected disease that the patient may have from among one or more candidate diseases based on the degree of susceptibility.

In the event that genetic information of a patient is input to the apparatus, the genetic information analyzer 111 may determine one or more candidate disease by using a genetic information-based disease susceptibility model database 114. A genetic information-based disease susceptibility model may be stored in the genetic information-based disease susceptibility model database 114. The genetic information-based disease susceptibility database 114 may be stored in a non-transitory computer readable recording medium or a memory. The genetic information-based disease susceptibility model is a pre-established model relating to correlation between analyzed genetic information of multiple patients and diagnosed diseases of these patients. The genetic information-based disease susceptibility model may include candidate diseases and a probability of each of the candidate diseases to be calculated based on visual information. The genetic information analyzer 111 may select a disease of the highest possibility among other candidate diseases, and may calculate a probability that the selected disease may be present in a patient.

In the event that EMR information of a patient is input to the apparatus for supporting acquisition of a multi-parametric MR image, the EMR analyzer 112 may select one or more candidate diseases with reference to the EMR-based disease susceptibility model database 115 so as to select a suspected disease that the patient may suffer from. An EMR-based disease susceptibility model is a model which has been established in advance by analyzing EMR information of a plurality of patients, and the model is stored in the EMR-based disease susceptibility model database 115.

If a user, such as a doctor, inputs a suspected body region or a suspected disease as diagnosis-aiding information, the diagnosis-aiding information analyzer 113 may analyze the diagnosis-aiding information to thereby determine one or more candidate diseases.

If a specific candidate disease satisfies a predetermined criterion among all the candidate diseases, the disease selector 110 may select the specific candidate disease as a suspected disease that the patient may suffer from. At this point, the predetermined criterion may be a probability of 50% or greater, and three candidate diseases may be selected as suspected diseases in descending order of a probability. Alternatively, a candidate disease input by a user or obtained from a CAD system may be selected as a suspected disease before others. For instance, the CAD system may provide the suspected disease to the disease selector by analyzing a previous medical image, such as an X-ray or MRI image, of a patient.

By using a multi-parametric MRI model, the image selector 120 may determine a set of imaging conditions of a multi-parametric MR image corresponding to a suspected disease. That is, the image selector 120 may determine a set of imaging conditions of a multi-parametric MR image corresponding to a suspected disease, by determining at least one of location, direction, distance, imaging order or imaging parameters of the multi-parametric MR image based on the multi-parametric MRI model. At this time, the multi-parametric MRI model includes an image type and an imaging order for each disease, which has been established by analyzing the priority of multi-parametric MR images for each disease. In addition, the multi-parametric MRI model may include details and imaging orders of multi-parametric MR images on a disease basis, and may be stored in the multi-parametric MRI model database 130.

Alternatively, the image selector 120 may determine a set of imagining conditions of a multi-parametric MR image based on patient medical information in short of determining a suspected disease. For example, the image selector 120 may determine the set of imaging conditions based on patient medical information such as diagnosis-aiding information, input by a user, a body region susceptible to a disease, or the detection of a suspected lesion or abnormality in a previous medical image of a patient in short of determining a suspected disease.

Figure 2A:
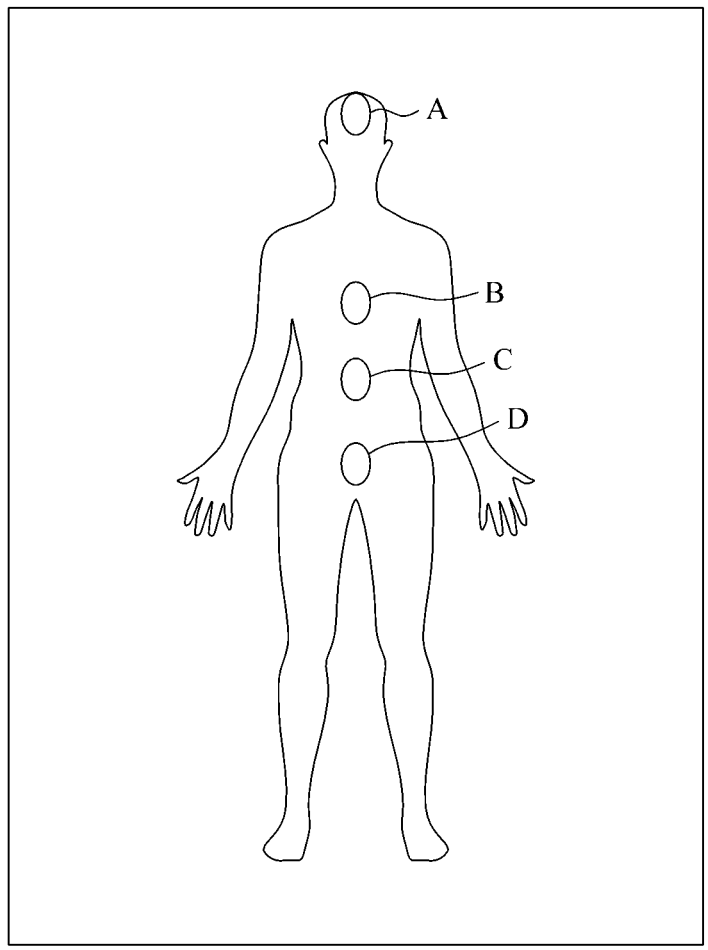
FIG. 2A is a diagram illustrating an operation of an example of a disease selector in an apparatus for supporting acquisition of a multi-parametric MR image.

FIG. 2A illustrates the operation of an example of a disease selector in an apparatus for supporting acquisition of a multi-parametric MR image.

In the event that genetic information of a patient is input to the apparatus for supporting acquisition of a multi-parametric MR image, the genetic information analyzer 111 may determine candidate diseases A, B, C and D and a probability that the patient has each of the candidate diseases A, B, C and D using a genetic information-based disease susceptibility model that is stored in the genetic information-based disease susceptibility model database 114. FIG. 2A illustrates candidate diseases A, B, C and D, which may have tendencies to occur at different locations of the body. For example, the candidate diseases A, B, C and D may be different types of cancer, and the genetic information may include genetic information that increases susceptibility of the patient to certain types of cancer. Table 1 provides the probabilities that the patient has the candidate diseases A, B, C and D.

TABLE 1

| Candidate disease | Probability |
|---|---|
| D | 94% |
| C | 42% |
| A | 16% |
| B | 11% |

In the event that the genetic information analyzer 111 determines the probabilities that a patient has candidate diseases A, B, C and D as illustrated in Table 1, the disease selector 110 may select candidate disease D as a suspected disease of the patient, based on a predetermined criterion. For example, the predetermined criterion may be having a probability of 50% or greater. In this example, the probability that the patient has candidate disease D is greater than 50%.

Figure 2B:
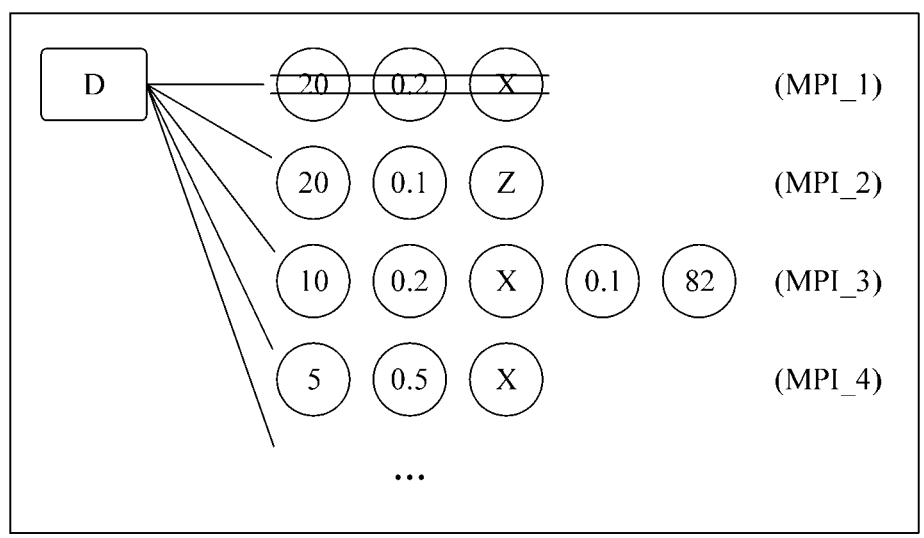
FIG. 2B is a diagrams illustrating an operation of an example of an image selector in an apparatus for supporting acquisition of a multi-parametric MR image.

FIG. 2B illustrates candidate a plurality of sets of imaging conditions that may be used to obtain a multi-parametric MR image.

By using a multi-parametric MRI model stored in the multi-parametric MRI model database 130, the image selector 120 may determine a set of imaging conditions of a multi-parametric MR image that corresponds to the suspected disease D. That is, the image selector 120 may determine a set of imaging conditions for each of one or more multi-parametric MR images MPI_1, MPI_2, MPI_3 and MPI_4 related to a suspected disease, by determining a location, a direction, a distance, a imaging order and imaging parameters of the multi-parametric MR image, as illustrated in FIG. 2B.

One or more sets of imaging conditions, which are selected by the image selector 120, may be stored in an imaging-ready image information database (not shown). An imaging device may capture a multi-parametric MR image based on a set of imaging conditions that is stored in the imaging-ready image database (now shown), transmit the captured multi-parametric MR image to a Computer-Aided Diagnosis (CAD) system, request the CAD system to analyze the captured multi-parametric MR image, and store the captured multi-parametric MR image in a capture-completed image information database (not shown). The CAD system may analyze the multi-parametric MR image acquired by the imaging device to thereby generate diagnostic data.

The imaging-ready image information database (not shown) and an imaging-completed image information database (not shown) may be included in an imaging device. However, the present disclosure is not limited thereto, and instead the imaging-ready image information database (not shown) and the imaging-completed image information database (not shown) may be included in an additional CAD system or the apparatus 100 for supporting acquisition of a multi-parametric MR image.

Figure 3:
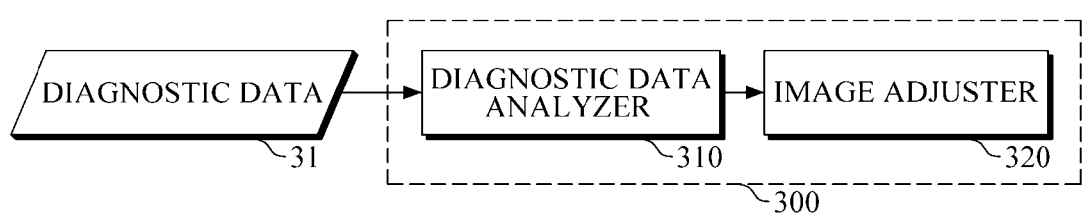
FIG. 3 is a block diagram illustrating another example of an apparatus for supporting acquisition of a multi-parametric MR image.

FIG. 3 is a block diagram illustrating another example of an apparatus for supporting acquisition of a multi-parametric MR image.

Referring to FIG. 3, an apparatus 300 for supporting acquisition of a multi-parametric MR image may include a diagnostic data analyzer 310 and an image adjuster 320.

The diagnostic data analyzer 310 receives diagnostic data 31 of a patient from a CAD system and analyzes the diagnostic data 31. When the imaging device captures a multi-parametric MR image relating to a suspected disease that patient may suffer from and transmits the captured multi-parametric image to the CAD system, the CAD system may analyze the captured multi-parametric image, generate the diagnostic data 31, and transmits the diagnostic data 31 to the diagnostic data analyzer 310. The diagnostic data 31 may include one or more candidate diseases, a body region susceptible to each of the candidate diseases, and a probability of each of the candidate diseases. The diagnostic data 31 may be transmitted from the CAD system in real time.

If the diagnostic data 31 is received, the diagnostic data analyzer 310 may analyze one or more candidate diseases and a probability of each of the candidate diseases, which are contained in the diagnostic data 31, and then may determine an additional set of imaging conditions for a multi-parametric MR image related to the suspected disease or select an additional suspected disease.

Figure 4:
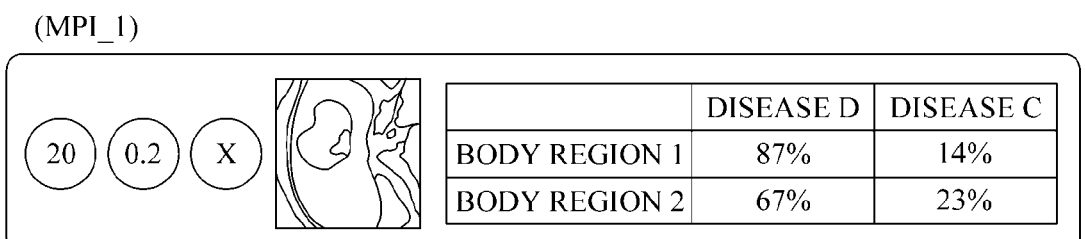
FIG. 4 is a view illustrating an example of diagnostic data which is input to an apparatus for supporting acquisition of a multi-parametric MR image.

For example, a CAD system may analyze a first multi-parametric MR image MPI-1 that is captured by an imaging device with respect to a body region 1 that is susceptible to a suspected disease D, and may generate diagnostic data, as illustrated in FIG. 4. In this example, if a body region 2 that is susceptible to the suspected disease D also satisfies a predetermined criterion of, for example, having a disease susceptibility of 50% or greater, the diagnostic data analyzer 310 may determine that it is necessary to select an additional multi-parametric MR image of the body region 2. In another example, if any one of body regions 1 and 2 that is susceptible to the disease C satisfies the predetermined criterion, the diagnostic data analyzer 310 may determine that it is necessary to select the disease C as an additional suspected disease.

Based on the analysis result from the diagnostic data analyzer 310, the image adjuster 320 may determine an additional set of imaging conditions for a multi-parametric MR image related to the suspected disease of the patient, or may adjust an existing set of imaging conditions thereof.

The additional set of imaging conditions or the adjusted set of imaging conditions may be transmitted to the imaging device to be stored in an imaging-ready image information database. As the additional set of imaging conditions may be determined in real time, in one example of the apparatus for supporting acquisition of a multi-parametric MR image, additional images of the patient may be obtained without removing the patient from an MRI device after taking the first multi-parametric MR image MPI-1. However, the present disclosure is not limited thereto.

Figure 5:
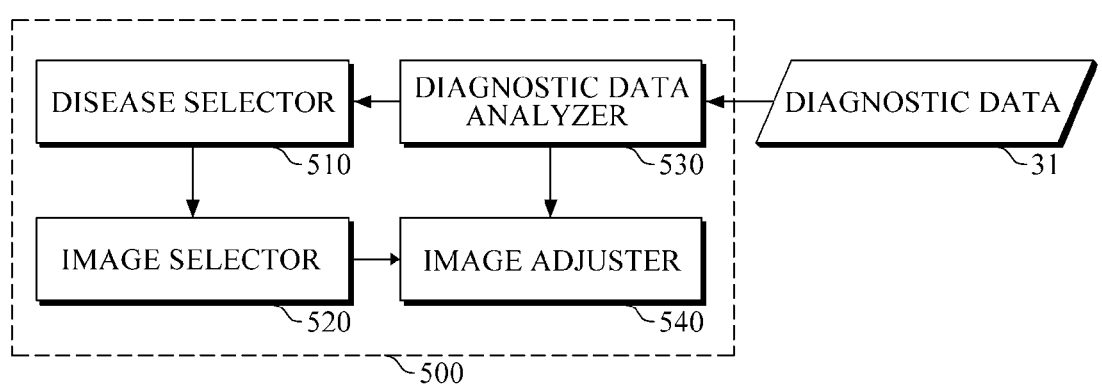
FIG. 5 is a block diagram illustrating yet another example of an apparatus for supporting acquisition of a multi-parametric MR image.

FIG. 5 is a block diagram illustrating yet another example of an apparatus for supporting acquisition of a multi-parametric MR image.

Examples of apparatuses for supporting acquisition of a multi-parametric MR image have been described above with reference to FIGS. 1 to 4. Hereinafter, another example of an apparatus for supporting acquisition of a multi-parametric MR image will be described. The description of various features of the example that is the same as the apparatuses shown in FIGS. 1 to 4 will be omitted for conciseness.

Referring to FIG. 5, an apparatus 500 for supporting acquisition of a multi-parametric MR image may include a disease selector 510, an image selector 520, a diagnostic data analyzer 530, and an image adjuster 540.

As described above with reference to FIG. 1, the disease selector 510 selects a suspected disease that a patient may suffer from, by analyzing patient information.

Once the disease selector 510 selects the suspected disease of the patient, the image selector 520 may determine a set of imaging conditions of a multi-parametric MR image that corresponds to the suspected disease based on a multi-parametric MRI model that has been established in advance.

The selected set of imaging conditions for the multi-parametric MR image related to the suspected disease may be stored in an imaging-ready-image information database of a capture device, such as an MRI scanner. In the event that the imaging device captures a multi-parametric MR image of the patient with reference to the imaging-ready image information database and then transmits the captured multi-parametric MR image to a CAD system, the CAD system may analyze the acquired multi-parametric MR image to thereby generate diagnostic data 31.

The diagnostic data analyzer 530 may receive the diagnostic data 31 from the CAD system, analyze the diagnostic data 31, and then determine whether to select an additional suspected disease that the patient may suffer from, or whether to determine an additional set of imaging conditions for a multi-parametric MR image related to an existing suspected disease, or whether to adjust an existing set of imaging conditions for a multi-parametric MR image related to an existing suspected disease.

Based on an analysis result from the diagnostic data analyzer 530, the image adjuster 540 may adjust the imaging conditions of a multi-parametric MR image related to a suspected disease. That is, according to an analysis result from the diagnostic data analyzer 530, the image adjuster 540 may determine an additional set of imaging conditions for a multi-parametric MR image related to an existing suspected disease or adjust an existing set of imaging conditions, determined by the image selector 520, for a multi-parametric MR image related to the existing suspected disease.

Alternatively, in the event that the diagnostic data analyzer 530 analyzes the diagnostic data 31 and then determines that it is necessary to select an additional suspected disease that the patient may suffer from, the disease selector 510 may select an additional suspected disease of the patient. In the event that the additional suspected disease is selected by the disease selector 510, the image selector 520 may determine a set of imaging conditions for a multi-parametric MR image related to the additional suspected disease.

In the event that image selector 520 selects a multi-parametric MR image related to an additional suspected disease, or in the event that the image adjuster 540 determines an additional set of imaging conditions or adjusts an existing set of imaging conditions for an MRI multi parametric images related to an existing suspected disease, the resultant information may be reflected in an imaging-ready image database of an imaging device. If the imaging device captures a multi-parametric MR image with reference to the imaging-ready image database in which the resultant information is stored, the CAD system may generate diagnostic data of the patient and transmit the diagnostic data to the diagnostic data analyzer 530.

Thus, when capturing a multi-parametric MR image of a patient, the apparatus 500 is capable of immediately utilizing the diagnostic data 31 received from the CAD system, along with information regarding a specific patient, which includes genetic information, EMR information and diagnosis-aiding information regarding the patient. In this way, the apparatus 500 is able to quickly acquire multi-parametric MR images with a high priority so that accuracy of diagnosis may be improved.

Figure 6:
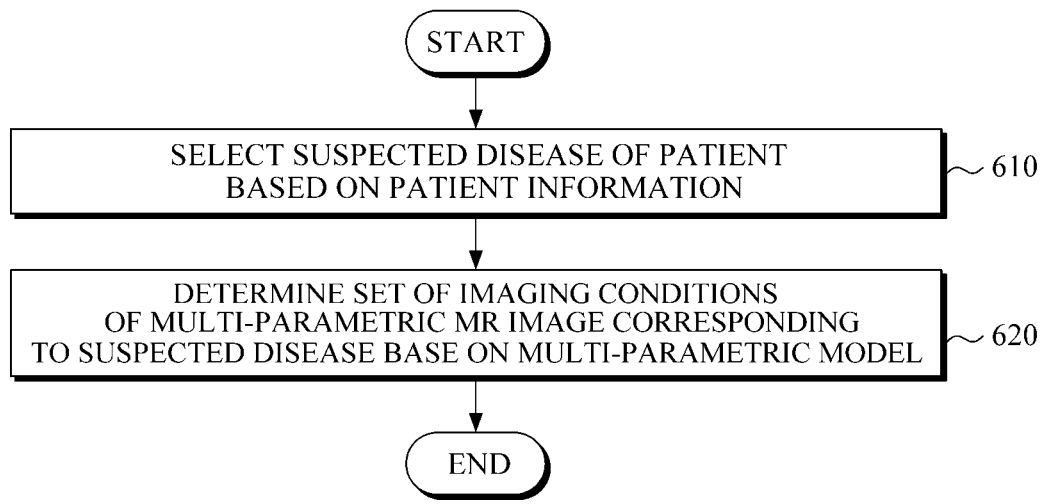
FIG. 6 is a flow chart illustrating an example of a method for supporting acquisition of a multi-parametric MR image using an apparatus shown in FIG. 1.

FIG. 6 is a flow chart illustrating a method for supporting acquisition of a multi-parametric MR image using an example of an apparatus illustrated in FIG. 1. Hereinafter, a method for supporting acquisition of a multi-parametric MR image using the apparatus 100 will be described with reference to FIG. 6. In addition, any description that has been provided above with reference to FIGS. 1 and 2B may be omitted herein for conciseness.

Referring to FIG. 6, in operation 610, the apparatus 100 analyzes information regarding a patient and selects a suspected disease that the patient may suffer from. For example, the operation of selecting the suspected disease may include an operation of determining one or more candidate diseases by analyzing the patient information and an operation of selecting a suspected disease based on the probability of each of the candidate diseases as determined by the disease selector 110.

In the operation of determining one or more candidate diseases, the apparatus 100 may determine one or more candidate diseases using a model that has been established in advance. For example, the model may have been established using genetic information of a plurality of patients and healthy people. In another example, the model may have been established in advance based on EMR information of a plurality of patients and healthy people, as described above with reference to FIG. 1. Alternatively, if diagnosis-aiding information, including a disease that is suspected based on examination of the patient, is input by a doctor, the apparatus 100 may determine the disease as a candidate disease.

In operation 620, the apparatus 100 may determine a set of imaging conditions of a multi-parametric MR image that corresponds to the suspected disease based on a multi-parametric MRI model. As illustrated in FIG. 2B, the apparatus 100 may determine a set of imaging conditions of a multi-parametric MR image corresponding to the suspected disease, by determining at least one of location, direction, distance, imaging order and imaging parameters of the multi-parametric MR image based on the multi-parametric MRI model.

Figure 7:
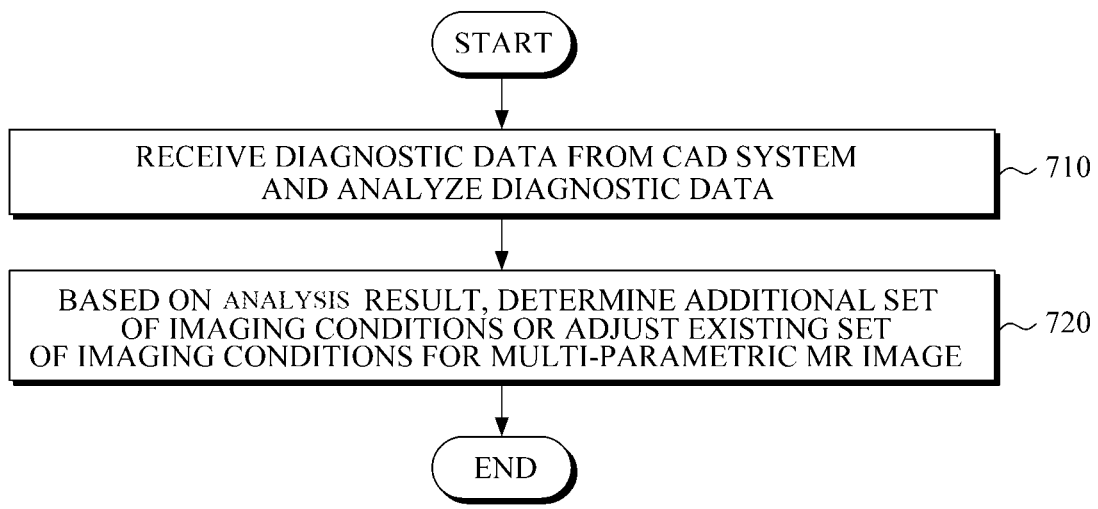
FIG. 7 is a flow chart illustrating an example of a method for supporting acquisition of a multi-parametric MR image using an apparatus shown in FIG. 3.

FIG. 7 is a flow chart illustrating a method for supporting acquisition of a multi-parametric MR image using an example of an apparatus illustrated in FIG. 3. Hereinafter, referring to FIG. 7, a method for supporting acquisition of a multi-parametric MR image using the apparatus 300 will be described. In addition, any description that has been provided in the above with reference to FIGS. 3 and 4 may be omitted for conciseness.

Referring to FIG. 7, in operation 710, the apparatus 300 receives diagnostic data from a CAD system. The diagnostic data may be a result obtained by the CAD system by analyzing a multi-parametric MR image related to a suspected disease that a patient may suffer from. The apparatus 300 may analyzes the received diagnostic data. As described in the above with reference to FIG. 3, the CAD system may transmit the diagnostic data to the apparatus 300 in real time.

In operation 720, based on the result of the analysis of the received diagnostic data, the apparatus 300 may determine an additional set of imaging conditions or adjust an existing set of imaging conditions for a multi-parametric MR image related to an existing suspected disease.

The additional set of imaging conditions or the adjusted set of imaging conditions may be stored in an imaging device. In the event that the imaging device obtains an additional multi-parametric MR image based on the additional or adjusted set of imaging conditions, the CAD system may analyze the additional multi-parametric MR image captured by the imaging device. In addition, a diagnostic data generated by the CAD system may be transmitted to the apparatus 300, so that accuracy of diagnosis may be improved.

FIG. 8 is a flow chart illustrating an example of a method for supporting acquisition of a multi-parametric MR image using an apparatus illustrated in FIG. 5. Hereinafter, referring to FIG. 8, a method for supporting acquisition of a multi-parametric MR image using the apparatus 500 will be described. In addition, any description that has been provided in the above with reference to FIG. 5 may be omitted for the sake of conciseness.

Referring to FIG. 8, in operation 810, the apparatus 500 analyzes information regarding a patient. The patient information may include genetic information, EMR information and diagnosis-aiding information of the patient that has been input directly by a doctor. In response to receiving the genetic information, the EMR information or the diagnosis-aiding information, the apparatus 500 may analyzes the received information to thereby determine one or more candidate diseases.

In operation 820, the apparatus 500 selects a suspected disease that the patient may suffer from among the candidate diseases in operation 820. The suspected disease may be selected based on a probability of each of the candidate diseases.

Next, once the suspected disease is selected, the apparatus 500 determines a set of imaging conditions of a multi-parametric MR image corresponding to the suspected disease based on a multi-parametric MRI model which has been established in advance, in operation 830. The determined set of imaging conditions for the multi-parametric MR image is transmitted to an imaging device.

In 840, the imaging device captures a multi-parametric MR image of the patient and transmits the captured multi-parametric MR image to a CAD system.

In response the CAD system analyzes the received multi-parametric MR image and generates diagnostic data. The apparatus 500 receives the diagnostic data from the CAD system and analyzes the diagnostic data in operation 850.

The CAD system may transmit the diagnostic data to the apparatus 500 in real time, and the diagnostic data may be used in the apparatus 500 when determining whether to select an additional suspected disease for the patient or whether to determine an additional set of imaging conditions for a multi-parametric MR image related to the suspected disease that is selected in operation 820.

Next, if it is determined in operation 860 that an additional suspected disease needs to be selected, the apparatus 500 may repeat operations 820, 830, 840, 850 and 860 sequentially.

Alternatively, if it is determined in operation 860 that an additional suspected disease does not need to be selected, the apparatus 500 may, in operation 870, determines whether to determine an additional set of imaging conditions or adjust the existing set of imaging conditions that is determined in operation 830, for a multi-parametric MR image related to the suspected disease that is selected in operation 820.

If the apparatus 500, in operation 870, determines that it is necessary to determine the additional set of imaging conditions or to adjust the existing set of imaging conditions, the additional set of imaging conditions are determined or the existing set of imaging conditions are adjusted in operation 880.

If the additional set of imaging conditions is determined or the existing set of imaging conditions are adjusted, the apparatus 500 may repeat operations 840, 850, 860, 870 and 880 sequentially to capture an additional multi-parametric MR image based on the additional set of imaging conditions or the adjusted set of imaging conditions.

In the event that a CAD system completed its analysis of a captured multi-parametric MR image of the patient, or in the event that a user requests to a termination of the diagnosing process, the apparatus 500 may terminate the diagnosing process. If not, the apparatus 500 may wait until receiving diagnostic data that is obtained by analyzing another multi-parametric MR image of the patient in the CAD system in operation 890.

In one example, in the event that the apparatus 500 selects an additional suspected disease, determines an additional set of imaging conditions for a multi-parametric MR image related to an existing suspected disease, or adjusts an existing set of imaging conditions for a multi-parametric MR image related to the existing suspected disease, the resultant information may be immediately reflected in an imaging device to select an additional suspected disease or capture an additional multi-parametric MR image. That is, the apparatus 500 may capture a multi-parametric MR image based on a set of imaging conditions, which is contained in the diagnostic data received from a CAD system, so that it is possible to accurately select a suspected disease that a patient may have and to acquire a more accurate multi-parametric MR image related to the suspected disease.

Described above are various examples of apparatuses and methods for supporting acquisition of an MR image. In one example, there is provided an apparatus for supporting acquisition of an MR image, including a disease selector configured to analyze information regarding the patient to select a suspected disease that a patient may be possibly suffering from; and an image selector configured to determine a set of imaging conditions of a multi-parametric MR image corresponding to the suspected disease based on a multi-parametric MRI model. The disease selector may analyze the information on the patient to determine to thereby determine one or more candidate diseases, and select the suspected disease based on a probability of each of the candidate diseases. The disease selector may include a genetic information analyzer configured to select one or more candidate diseases using a disease susceptibility model which has been established in advance based on genetic information of the patient. The disease selector may include an EMR analyzer configured to select one or more candidate diseases using a disease susceptibility model which has been established in advance based on EMR information of the patient. The disease selector may include a diagnosis-aiding information analyzer configured to select one or more candidate diseases based on diagnosis-aiding information input by a user. The image selector may determines the set of imaging conditions by determining at least one of location, direction, distance, imaging order and imaging parameters of the MRI multi-parametric image based on the multi-parametric MRI model. The multi-parametric MRI model may be a model that includes an image type and an imaging order for each disease, which has been established by analyzing the priority of multi-parametric MR images for each disease.

Another example of an apparatus for supporting acquisition of an MR image may include a diagnostic data analyzer configured to receive diagnostic data which a CAD system generates by analyzing a captured multi-parametric MR image related to a suspected disease that a patient possibly suffer, and to analyze the received diagnostic data; and an image adjuster configured to, according to an analysis result from the diagnostic data analyzer, determine an additional set of imaging conditions or adjust an existing set of imaging conditions for a multi-parametric MR image related to the suspected disease.

The diagnostic data analyzer may receive the diagnostic data from the CAD system in real time. The diagnostic data may include body regions respectively susceptible to one or more diseases and a disease susceptibility of each of the body regions.

Another example of an apparatus for supporting acquisition of an MR image may include a disease selector configured to analyze information on the patient to thereby select a suspected disease that a patient possibly suffer from; an image selector configured to determine a set of imaging conditions of a multi-parametric MR image corresponding to the suspected disease based on a multi-parametric MRI model; a diagnostic data analyzer configured to receive diagnostic data which a CAD system generates by analyzing the selected multi-parametric MR image, and to analyze the received diagnostic data; and an image adjuster configured to, according to an analysis result from the diagnostic data analyzer, adjust the multi-parametric MR image related to the suspected disease.

The image adjuster may determine an additional set of imaging conditions for the multi-parametric MR image related to the suspected disease according to the analysis result. The image adjuster may be configured to adjust an existing set of imaging conditions for the multi-parametric MR image related to the suspected disease according to the analysis result. The disease selector may, according to the analysis result select an additional suspected disease that the patient possibly suffer, and the image selector selects a multi-parametric MR image related to the additional suspected disease. The information on the patient may include at least one among genetic information, EMR information and diagnosis-aiding information, input by a user, of the patient.

There is also provided an example of a method for supporting acquisition of an MR image. The example may involve selecting a suspected disease that a patient possibly suffer from, by analyzing information on the patient; and determining a set of imaging conditions of a multi-parametric MR image corresponding to the suspected disease based on a multi-parametric MRI model. The selecting of the suspected disease may include determining one or more candidate diseases by analyzing the information on the patient; and selecting the suspected disease based on a probability of each of the candidate diseases. The determination of one or more candidate diseases may include selecting one or more candidate diseases based on a disease susceptibility model which has been established based on genetic information. The determination of one or more candidate diseases may include determining one or more candidate diseases based on a disease susceptibility model which has been established based on EMR document. The determination of one or more candidate diseases may include determining one or more candidate diseases based on diagnosis-aiding information input by a user.

The selection of the multi-parametric MR image may include determining at least one of location, direction, distance, imaging order and imaging parameters of the multi-parametric MR image. The multi-parametric MRI model may include an image type and an imaging order for each disease, which has been established by analyzing the priority of multi-parametric MR images for each disease.

Another example of a method for supporting acquisition of a multi-parametric MR image may involve: receiving from a CAD system diagnostic data which is a result of analyzing an acquired multi-parametric MR image suitable for a suspected disease that a patient possibly suffer from, and analyzing the diagnostic data; and according to an analysis result of the diagnostic data, determining an additional set of imaging conditions for the multi-parametric MR image or adjusting an existing set of imaging conditions for the multi-parametric MR image. The analysis of the diagnostic data may include receiving the diagnostic data from the CAD system in real time. The diagnostic data may include body regions susceptible to one or more diseases and a disease susceptibility of each of the body regions.

Another example of a method for supporting acquisition of a multi-parametric MR image may involve: selecting a suspected disease that a patient possibly suffer from, by analyzing information on the patient; determining a set of imaging conditions of a multi-parametric MR image corresponding to the suspected disease based on a multi-parametric MRI model; receiving from a CAD system diagnostic data which is a result of analyzing the multi-parametric MR image, and analyzing the diagnostic data; and adjusting the multi-parametric MR image corresponding to the suspected disease based on an analysis result of the diagnostic data. The adjusting of the multi-parametric MR image may include, according to an analysis result of the diagnostic data, determining an additional set of imaging conditions for the multi-parametric MR image related to the suspected disease.

The adjusting of the multi-parametric MR image may include, according to an analysis result of the diagnostic data, adjusting the determined set of imaging conditions for the multi-parametric MR image related to the suspected disease. The selecting of the additional suspected disease may include, according to the analysis result of the information on the patient, determining the additional suspected disease of the patient, and the determining of the set of imaging conditions comprises determining a set of imaging conditions for a multi-parametric MR image related to the additional suspected disease.

The information on the patient may include at least one among genetic information, EMR information and diagnosis-aiding information, input by a user, on the patient.

The apparatuses, units, selectors, and analyzers described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The methods described above may be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums.

The media may also include, alone or in combination with the software program instructions, data files, data structures, and the like. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). The databases described herein may be stored in a non-transitory computer readable recording medium or a memory. In addition, functional programs, codes, and code segments for accomplishing the example disclosed herein can be construed by programmers skilled in the art based on the flow diagrams and block diagrams of the figures and their corresponding descriptions as provided herein.

While this disclosure includes specific examples, it will be apparent to one of ordinary skill in the art that various changes in fond and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for supporting acquisition of magnetic resonance (MR) images, the apparatus comprising:
   a memory, configured to store instructions; and
   at least one processor, upon executing the stored instructions, being configured to:
   determine one or more candidate diseases of a suspected disease of a patient and calculate a probability that the patient has each of the one or more candidate diseases based on patient information and information on previously diagnosed diseases of a plurality of patients, determine a candidate disease as the suspected disease among the one or more candidate diseases based on the probability,
   determine, according to the candidate disease, a set of imaging device control values for capturing an MR image related to the candidate disease, and
   transmit, to an imaging device, the determined set of imaging device control values such that the imaging device captures the MR image using the determined set of imaging device control values,
   wherein the patient information comprises at least one of patient genetic information, electronic medical record (EMR) information, or diagnosis-aiding data input by a user.

2. The apparatus of claim 1,
   wherein the set of imaging device control values includes at least one of a location, a direction, a distance, an imaging order, or imaging parameters of the MR image, and
   wherein the at least one processor is further configured to determine the set of imaging device control values according to the candidate disease based on an MRI model.

3. The apparatus of claim 2, wherein the MRI model comprises an image type and an imaging order for each disease, the MRI model being established in advance by analyzing a priority of MR images for each disease.

4. An apparatus for supporting acquisition of magnetic resonance (MR) images, the apparatus comprising:
   a memory, configured to store instructions; and
   at least one processor, upon executing the stored instructions, being configured to:
   determine one or more candidate diseases of a suspected disease of a patient and calculate a probability that the patient has each of the one or more candidate diseases based on patient information and information on previously diagnosed diseases of a plurality of patients,
   determine a candidate disease as the suspected disease among the one or more candidate diseases based on the probability,
   receive diagnostic data generated by a computer aided diagnosis (CAD) system by analyzing a captured first MR image,
   analyze the received diagnostic data,
   determine, based on an analysis result of the received diagnostic data, an additional set of imaging device control values or adjust an existing set of imaging device control values for capturing a second MR image related to an additional suspected disease, the additional set of imaging device control values or the existing set of imaging device control values being determined according to the additional suspected disease, and
   transmit, to an imaging device, the determined additional set of imaging device control values or the adjusted existing set of imaging device control values such that the imaging device captures the second MR image using the determined additional set of imaging device control values or the adjusted existing set of imaging device control values,
   wherein the patient information comprises at least one of patient genetic information, electronic medical record (EMR) information, or diagnosis-aiding data input by a user.

5. The apparatus of claim 4, wherein the at least one processor is further configured to receive the diagnostic data from the CAD system in real time.

6. The apparatus of claim 4, wherein the diagnostic data comprises body regions susceptible to one or more diseases and a disease susceptibility of each of the body regions.

7. An apparatus for supporting acquisition of magnetic resonance (MR) images, the apparatus comprising:
   a memory, configured to store instructions; and
   at least one processor, upon executing the stored instructions, being configured to:
   determine one or more candidate diseases of a suspected disease of a patient and calculate a probability that the patient has each of the one or more candidate diseases based on patient information and information on previously diagnosed diseases of a plurality of patients,
   determine a candidate disease as the suspected disease among the one or more candidate diseases,
   determine, according to the candidate disease, a set of imaging device control values for capturing a first MR image related to the candidate disease based on an MRI model,
   receive diagnostic data generated by a computer aided diagnosis (CAD) system by analyzing the first MR image,
   analyze the received diagnostic data,
   select, based on an analysis result of the received diagnostic data, an additional suspected disease and adjust the set of imaging device control values for capturing a second MR image related to the additional suspected disease, and
   transmit, to an imaging device, the adjusted set of imaging device control values such that the imaging device captures the second MR image using the adjusted set of imaging device control values,
   wherein the patient information comprises at least one of patient genetic information, electronic medical record (EMR) information, or diagnosis-aiding data input by a user.

8. The apparatus of claim 7, wherein the at least one processor is further configured to determine an additional set of imaging device control values for capturing the second MR image related to the additional suspected disease according to the analysis result.

9. The apparatus of claim 7, wherein the at least one processor is further configured to adjust an existing set of imaging device control values for capturing the second MR image related to the additional suspected disease according to the analysis result.

10. The apparatus of claim 7, wherein the at least one processor is further configured to determine an additional set of imaging device control values for capturing the second MR image related to the additional suspected disease.

11. An apparatus for supporting acquisition of magnetic resonance (MR) images, the apparatus comprising:
a memory, configured to store instructions; and
at least one processor, upon executing the stored instructions, being configured to:
determine one or more candidate diseases of a suspected disease of a patient and calculate a probability that the patient has each of the one or more candidate diseases based on patient information and information on previously diagnosed diseases of a plurality of patients,
determine a candidate disease as the suspected disease among the one or more candidate diseases based on the probability,
determine, according to the candidate disease, a set of imaging device control values for capturing an MR image related to the candidate disease of the patient using a database that associates imaging device control values with medical conditions, and
transmit, to an imaging device, the determined set of imaging device control values such that the imaging device captures the MR image using the determined set of imaging device control values,
wherein the patient information comprises at least one of patient genetic information, electronic medical record (EMR) information, or diagnosis-aiding data input by a user.

12. The apparatus of claim 11, wherein the set of imaging device control values comprises at least one selected from a group consisting of a location, a direction, a distance, an imaging order, and imaging parameters for capturing the MR image.

13. A method for supporting acquisition of magnetic resonance (MR) images, the method comprising:
determining one or more candidate diseases of a suspected disease of a patient and calculating a probability that the patient has each of the one or more candidate diseases based on patient information and information on previously diagnosed diseases of a plurality of patients;
determining a candidate disease as the suspected disease among the one or more candidate diseases based on the probability;
determining, according to the candidate disease, a set of imaging device control values for capturing an MR image related to the candidate disease; and
transmitting, to an imaging device, the determined set of imaging device control values such that the imaging device captures the MR image using the determined set of imaging device control values,
wherein the patient information comprises at least one of patient genetic information, electronic medical record (EMR) information, or diagnosis-aiding data input by a user.

14. The method of claim 13,
wherein the patient information comprises diagnosis-aiding data input by the user, and
wherein the determination of the one or more candidate diseases comprises determining the one or more candidate diseases based on the diagnosis-aiding data.

15. The method of claim 13, wherein the set of imaging device control values comprises at least one of a location, a direction, a distance, an imaging order or imaging parameters of the MR image.

16. The method of claim 13, wherein an MRI model comprises an image type and an imaging order for each disease, the MRI model being established in advance by analyzing a priority of MR images for each disease.

17. A method for supporting acquisition of magnetic resonance (MR) images, the method comprising:
determining one or more candidate diseases of a suspected disease of a patient and calculating a probability that the patient has each of the one or more candidate diseases based on patient information and information on previously diagnosed diseases of a plurality of patients;
determining a candidate disease as the suspected disease among the one or more candidate diseases based on the probability;
receiving diagnostic data obtained by analyzing an acquired first MR image from a computer aided diagnosis (CAD) system;
analyzing the diagnostic data;
determining, based on an analysis result of the diagnostic data, an additional set of imaging device control values for capturing a second MR image or adjusting an existing set of imaging device control values for capturing the second MR image related to an additional suspected disease, the additional set of imaging device control values or the existing set of imaging device control values being determined according to the additional suspected disease; and
transmitting, to an imaging device, the determined additional set of imaging device control values or the adjusted existing set of imaging device control values such that the imaging device captures the second MR image using the determined additional set of imaging device control values or the adjusted existing set of imaging device control values,
wherein the patient information comprises at least one of patient genetic information, electronic medical record (EMR) information, or diagnosis-aiding data input by a user.

18. The method of claim 17, wherein the receiving of the diagnostic data comprises receiving the diagnostic data from the CAD system in real time.

19. The method of claim 17, wherein the diagnostic data comprises body regions susceptible to one or more diseases and a disease susceptibility of each of the body regions.

20. A method for supporting acquisition of magnetic resonance (MR) images, the method comprising:
determining one or more candidate diseases of a suspected disease of a patient and calculating a probability that the patient has each of the one or more candidate diseases based on patient information and information of previously diagnosed diseases of a plurality of patients;
determining a candidate disease as the suspected disease among the one or more candidate diseases;
determining, according to the candidate disease, a set of imaging device control values for capturing a first MR image related to the candidate disease based on an MRI model;
receiving diagnostic data obtained by analyzing the first MR image from a computer aided diagnosis (CAD) system;
analyzing the diagnostic data;

determining an additional suspected disease based on an analysis result of the diagnostic data;

adjusting the set of imaging device control values for capturing a second MR image related to the additional suspected disease; and transmitting, to an imaging device, the adjusted set of imaging device control values such that the imaging device captures the second MR image using the adjusted set of imaging device control values, wherein the patient information comprises at least one of patient genetic information, electronic medical record (EMR) information, or diagnosis-aiding data input by a user.

21. The method of claim 20, wherein adjusting of the set of imaging device control values for capturing a third MR image comprises determining an additional set of imaging device control values for the second MR image related to the additional suspected disease.

22. The method of claim 20, wherein the adjusting of the set of imaging device control values for capturing the second MR image comprises adjusting the set of imaging device control values for the first MR image related to the candidate disease.

23. A method for supporting acquisition of magnetic resonance (MR) images, the method comprising:

determining candidate diseases of a suspected disease of a patient and calculating a probability that the patient has each of the one or more candidate diseases based on patient information and information on previously diagnosed diseases of a plurality of patients;

determining a candidate disease as the suspected disease among the one or more candidate diseases;

determining, according to the candidate disease, a set of imaging device control values for capturing an MR image related to the candidate disease using a database stored in a memory; and transmitting, to an imaging device, the determined set of imaging device control values such that the imaging device captures the MR image using the determined set of imaging device control values, wherein the patient information comprises at least one of patient genetic information, electronic medical record (EMR) information, or diagnosis-aiding data input by a user.

24. The method of claim 23, wherein the set of imaging device control values comprises at least one selected from a group consisting of a location, a direction, a distance, an imaging order, and imaging parameters for capturing the MR image.

25. The method of claim 23, further comprising:

analyzing the obtained MR image of the patient to either adjust the determined set of imaging device control values or to select another set of imaging device control values; and obtaining a further MR image of the patient using the adjusted set of imaging device control values or the another set of imaging device control values.

\* \* \* \* \*